United States Patent [19]

Castrogiovanni et al.

[11] Patent Number: 5,505,937
[45] Date of Patent: Apr. 9, 1996

[54] COSMETIC COMPOSITIONS WITH IMPROVED TRANSFER RESISTANCE

[75] Inventors: Anthony Castrogiovanni, Belford, N.J.; Salvatore J. Barone, Staten Island, N.Y.; Ann Krog, Red Bank, N.J.; Marion L. McCulley, South River, N.J.; Joseph F. Callelo, Union, N.J.

[73] Assignee: Revlon Consumer Products Corporation, New York, N.Y.

[21] Appl. No.: 470,329

[22] Filed: Jun. 27, 1995

Related U.S. Application Data

[63] Continuation of Ser. No. 287,586, Aug. 8, 1994, abandoned, which is a continuation of Ser. No. 990,716, Dec. 15, 1992, abandoned.

[51] Int. Cl.$^6$ ................................. A61K 7/027
[52] U.S. Cl. ................. 424/64; 424/63; 424/401; 424/DIG. 5; 514/772.3; 514/787
[58] Field of Search ................. 424/63, 64, 401, 424/DIG. 5; 514/772.3, 787

[56] References Cited

U.S. PATENT DOCUMENTS

| | | |
|---|---|---|
| 4,486,405 | 12/1984 | Klein . |
| 4,574,082 | 3/1986 | Tietjen et al. . |
| 4,725,495 | 2/1988 | Garbe et al. . |
| 4,777,041 | 10/1988 | Mercado . |
| 4,792,444 | 12/1988 | Fukasawa et al. . |
| 4,839,163 | 6/1989 | Busch, Jr. . |
| 4,873,078 | 10/1989 | Edmundson et al. . |
| 4,980,167 | 12/1990 | Harashima et al. . |
| 4,992,477 | 2/1991 | Geria . |
| 5,011,680 | 4/1991 | Suzuki et al. . |
| 5,015,469 | 5/1991 | Yoneyama et al. . |
| 5,036,108 | 7/1991 | Asahi et al. . |
| 5,061,481 | 10/1991 | Suzuki et al. . |
| 5,085,856 | 2/1992 | Dunphy et al. . |
| 5,089,256 | 2/1992 | Scheller et al. . |
| 5,093,111 | 3/1992 | Baker et al. . |
| 5,106,611 | 4/1992 | Forestier et al. . |
| 5,118,496 | 6/1992 | Herstein . |
| 5,126,126 | 6/1992 | Varaprath et al. . |
| 5,141,741 | 8/1992 | Ishida et al. . |
| 5,143,722 | 9/1992 | Hollenberg et al. . |
| 5,143,723 | 9/1992 | Calvo et al. . |
| 5,208,012 | 5/1993 | Sudo et al. . |
| 5,210,251 | 5/1993 | Ohashi et al. . |
| 5,213,716 | 5/1993 | Patel et al. . |
| 5,213,799 | 5/1993 | Göring et al. . |
| 5,219,560 | 6/1993 | Suzubi et al. . |
| 5,225,186 | 7/1993 | Castrogiovanni et al. . |
| 5,234,682 | 8/1993 | Macchio et al. . |
| 5,262,087 | 11/1993 | Tachibana et al. . |
| 5,266,321 | 11/1993 | Shukuzaki et al. . |
| 5,288,482 | 2/1994 | Krzysik . |
| 5,292,530 | 3/1994 | McCrea et al. . |
| 5,302,382 | 4/1994 | Kasprzak . |
| 5,310,547 | 6/1994 | Dunphy et al. . |
| 5,318,775 | 6/1994 | Shore et al. . |
| 5,324,506 | 5/1994 | Calvo et al. . |
| 5,334,372 | 8/1994 | Kawamata et al. . |
| 5,338,536 | 8/1994 | Thimineur et al. . |
| 5,340,569 | 8/1994 | Elliott et al. . |
| 5,346,642 | 9/1994 | Patel et al. . |
| 5,362,482 | 11/1994 | Yoneyama et al. . |
| 5,364,633 | 11/1994 | Hill et al. . |
| 5,380,527 | 1/1995 | LeGrow et al. . |
| 5,382,433 | 1/1995 | Pahlck et al. . |
| 5,385,730 | 1/1995 | Ichinohe . |
| 5,387,417 | 2/1995 | Bentsch . |
| 5,389,365 | 2/1995 | LeGrow et al. . |
| 5,397,566 | 3/1995 | Thimineur et al. . |
| 5,412,004 | 5/1995 | Tachibana et al. . |

FOREIGN PATENT DOCUMENTS

| | | |
|---|---|---|
| 0005922 | 12/1979 | European Pat. Off. . |
| 0133963 | 3/1985 | European Pat. Off. . |
| 0179416 | 4/1986 | European Pat. Off. . |
| 0200839 | 12/1986 | European Pat. Off. . |
| 0205961 | 12/1986 | European Pat. Off. . |
| 0255655 | 2/1988 | European Pat. Off. . |
| 0272832 | 6/1988 | European Pat. Off. . |
| 0381166 | 8/1990 | European Pat. Off. . |
| 0504966 | 9/1992 | European Pat. Off. . |
| 1301966 | 7/1962 | France . |
| 1031966 | 7/1962 | France . |
| 2556940 | 6/1985 | France . |
| 1012730 | 7/1957 | Germany . |
| 967031 | 9/1957 | Germany . |
| 1018194 | 10/1957 | Germany . |
| 968535 | 5/1958 | Germany . |
| 3744352 | 7/1989 | Germany . |
| 3837473 | 5/1990 | Germany . |
| 317302 | 12/1956 | Switzerland . |
| 1476195 | 6/1977 | United Kingdom . |
| 1476194 | 6/1977 | United Kingdom . |
| 1569009 | 6/1980 | United Kingdom . |
| 2107186 | 4/1983 | United Kingdom . |
| 9112793 | 9/1990 | WIPO . |

*Primary Examiner*—Thurman K. Page
*Attorney, Agent, or Firm*—Julie Blackburn

[57] ABSTRACT

A transfer resistant cosmetic composition comprising:

a) 1–70% volatile solvent b) 0.1–15% silicone resin c) 10–45% wax d) 5–50% powder e) 1–30% oil

33 Claims, No Drawings

COSMETIC COMPOSITIONS WITH IMPROVED TRANSFER RESISTANCE

This is a continuation of application Ser. No. 287,586 filed Aug. 8, 1994, which is in turn a continuation of Ser. No. 990,716, filed Dec. 15, 1992, both now abandoned.

TECHNICAL FIELD

The invention is in the field of cosmetic makeup compositions for application to lips and skin.

BACKGROUND OF THE INVENTION

Cosmetic compositions are generally defined as compositions suitable for application to the human body. Cosmetic compositions such as creams and lotions are used to moisturize skin and keep it in a smooth supple condition. Pigmented cosmetic compositions such as makeup, blush, lipstick, etc. are used color to the skin and lips. Since color is one of the most important reasons for wearing cosmetics, color containing cosmetics must be very carefully formulated to provide maximum wear and effect.

One of the long standing problems with makeup, particularly lipstick, is the tendency of the cosmetic to blot or transfer from the skin onto other surfaces such as glassware, silverware, clothing, etc. This not only creates soiling on implements, but forces the lipstick user to reapply the cosmetic at fairly short intervals in order to keep the lips colored.

The object of the invention is to formulate a cosmetic composition for application to skin or lips which exhibits superior transfer resistance when compared with traditional makeup formulations.

SUMMARY OF THE INVENTION

The invention is directed to a cosmetic composition comprising, by weight of the total composition:

a) 1–70% of a volatile solvent
b) 0.1–15% silicone resin
c) 10–45% wax
d) 5–50% powder
e) 1–30% oil The composition of the invention provides a cosmetic composition which exhibits superior transfer resistance.

DETAILED DESCRIPTION

The term "volatile" means that the solvent has a measurable vapor pressure. The volatile solvents of the invention generally have a low viscosity, ranging from about 0.5 to 20 centipoise at 25° C. Volatile solvents suitable in the composition of the invention include volatile low viscosity silicone fluids such as cyclic silicones having the general formula:

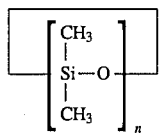

wherein n=3–7. Volatile linear polydimethylsiloxanes are also suitable and generally have from about 3 to 9 silicon atoms and are of the formula:

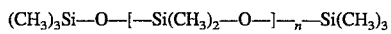

wherein n=0–7. These silicones are available from various sources including Dow Corning Corporation, General Electric, etc. The Dow Corning cyclic silicones are sold under the tradenames Dow Corning 244, 245, 344, 345, and 200 fluids. These fluids comprise octamethylcyclotetrasiloxane, decamethylcyclopentasiloxane, hexamethyldisiloxane, or mixtures thereof. Also suitable as the volatile solvent component are various $C_8$–$C_{20}$ isoparaffins such as $C_{12}$ isoparaffin made by The Permethyl Corporation having the tradename Permethyl® 99A, or a $C_{12}$ isoparaffin (isododecane) distributed by Presperse having the trade name Permethyl 99A. Various $C_{16}$ isoparaffins commercially available, such as isohexadecane (having the tradename Permethyl®) are also suitable. It is generally preferred that the volatile solvent component be a mixture of volatile silicones and $C_{8-20}$ isoparaffins. A ratio of 1:1 to about 4:1, respectively is suggested. The preferred formulation of the invention comprises 35–60% of a volatile solvent component comprised of a 1:1 to about 4:1 ratio of cyclic silicones and $C_{8-20}$ isoparaffins.

The silicone resins used in the composition of the invention of the invention are silicone ester waxes comprising moieties of the general formula:

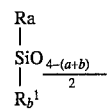

wherein R is hydrogen or an organic radical, $R^1$ is a carboxylic ester containing radical having at least 12 carbon atoms, a is an integer from 0 to 3 inclusive, and the sum of a+b has an average value of from about 1.0 to about 3.0 with the proviso that there is present at least one $R^1$ radical. The silicone ester waxes are liquids, or solids having a melting point of up to 90° C. Preferably, the $R^1$ radical comprises an ester group having a fatty acid moiety of 12–18 carbon atoms. In the preferred embodiment the $R^1$ radical is an isostearoyl ester. The preferred formulation of the invention comprises 3–10% of silicone ester such as waxes lauryl trimethylolpropane siloxy silicate (also called dilaurolyl trimethylolpropane siloxy silicate), and isostearyl trimethylolpropane siloxy silicate (also called diisostearoyl trimethylolpropane siloxy silicate). Dilauroyl trimethylolpropane siloxy silicate is the silicone polymer that conforms generally to the formula:

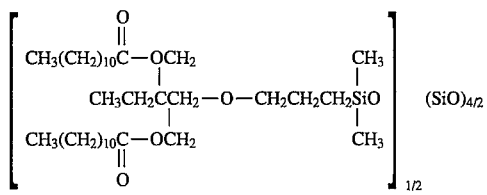

Diisostearoyl trimethylolpropane siloxy silicate is the silicone polymer that conforms generally to the formula:

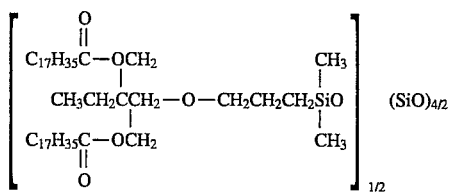

The waxes or wax-like materials of the invention generally have a melting point range of 35°–120° C. Waxes in this category include synthetic wax, ceresin, paraffin, ozokerite, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, or mixtures thereof. The preferred formulation of the invention comprises about 10–30% of a mixture of waxes.

The powder component of the invention can be generally defined as dry, particulate matter having a particle size of 0.02–50 microns. The particulate matter may be colored or non-colored (for example white). Suitable powders include bismuth oxychloride, titanated mica, fumed silica, spherical silica beads, polymethylmethacrylate beads, micronized teflon, boron nitride, acrylate polymers, aluminum silicate, aluminum starch octenylsuccinate, bentonite, calcium silicate, cellulose, chalk, corn starch, distomaceous earth, fuller's earth, glyceryl starch, hectorite, hydrated silica, kaolin, magnesium aluminum silicate, magnesium carbonate, magnesium hydroxide, magnesium oxide, magnesium silicate, magnesium trisilicate, maltodextrin, montmorillonite, microcrystalline cellulose, rice starch, silica, talc, mica, titanium dioxide, zinc laurate, zinc myristate, zinc neodecanoate, zinc rosinate, zinc stearate, polyethylene, alumina, attapulgite, calcium carbonate, calcium silicate, dextran, kaolin, nylon, silica silylate, silk powder, serecite, soy flour, tin oxide, titanium hydroxide, trimagnesium phosphate, walnut shell powder, or mixtures thereof. The above mentioned powders may be surface treated with lecithin, amino acids, mineral oil, silicone oil, or various other agents either alone or in combination, which coat the powder surface and render the particles hydrophobic in nature.

The powder component also comprises various organic and inorganic pigments. The organic pigments are generally various aromatic types including azo, indigoid, triphenylmethane, anthraquinone, and xanthine dyes which are designated as D&C and FD&C blues, browns, greens, oranges, reds, yellows, etc. Inorganic pigments generally consist of insoluble metallic salts of certified color additives, referred to as the Lakes or iron oxides.

Obviously the percentage of pigments used in the powder component will depend upon the type of cosmetic being formulated. Blushes, eyeshadows, lipsticks and similar cosmetics will contain higher percentages of pigment in the powder phase, usually ranging from 5–50% of the total cosmetic composition. Generally, the powder:pigment ratio ranges from 1:20 to 20:1. The preferred embodiment of the invention comprises 10–30% of a powder component wherein the powder component comprises about 10–20% of the total composition and the pigment component comprises 1–10% of the total composition.

The composition of the invention also contains oils, preferably a mixture of low viscosity and high viscosity oils. Suitable low viscosity oils have a viscosity of 5 to 100 centipoise at 25° C., and are generally esters having the structure RCO-OR' wherein RCO represents the carboxylic acid radical and wherein OR' is an alcohol residue. Examples of these low viscosity oils include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, cocodicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or mixtures of octyldodecanol, acetylated lanolin alcohol, cetyl acetate, isododecanol, polyglyceryl-3-diisostearate, or mixtures thereof. The high viscosity surface oils generally have a viscosity of 200–1,000,000 centipoise at 25° C., preferably a viscosity of 100,000–250,000 centipoise. Surface oils include castor oil, lanolin and lanolin derivatives, triisocetyl citrate, sorbitan sesquioleate, $C_{10-18}$ triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or mixtures thereof.

The suggested ratio of low viscosity to high viscosity oils in the oil phase is 1:15 to 15:1, preferably 1:10 to 10:1 respectively. The preferred formulation of the invention comprises 1–20% of a mixture of low viscosity and high viscosity surface oils.

Other ingredients may also be added to the above composition including various types of amorphous polypropylene, preservatives, antioxidants, and the like. The suggested range of amorphous or atactic polypropylene is about 0.1–10%. Suitable polypropylenes are described in U.S. patent application Ser. No. 895,065 filed Jun. 8, 1992 now U.S. Pat. No. 5,392,380, which is hereby incorporated by reference.

It may be desireable to add various preservatives such as the parabens, BHT, BHA, etc. Generally, 0.01–5% preservative is suggested.

The cosmetic compositions according to the invention provide a unique finish which exhibits superior transfer resistance when compared with normal cosmetic compositions. The term "transfer resistance" means that when the cosmetic composition is applied to skin or lips it exhibits from 10–100%, preferably 30–100% improvement in transfer resistance when compared with a standard lipstick formulation and as measured by the Kiss test of Example 4.

The invention will be further described in connection with the following examples which are set forth for the purposes of illustration only.

EXAMPLE 1

A transfer resistant lipstick composition with shine was made according to the following formula:

|  | w/w% | |
| --- | --- | --- |
|  | (a) | (b) |
| Synthetic wax | 6.00 | 6.60 |
| Ceresin | 4.00 | 4.00 |
| Paraffin | 3.00 | 3.00 |
| Isododecane | 10.00 | 10.00 |
| Cetyl acetate/acetylated lanolin alcohol | 5.00 | 5.00 |
| Methyl paraben | .30 | .30 |

-continued

|  | w/w% | |
|---|---|---|
|  | (a) | (b) |
| Propyl paraben | .10 | .10 |
| BHA | .10 | .10 |
| Red #7 Calcium Lake | 4.00 | 3.00 |
| Yellow 5 Aluminum Lake | 3.00 | — |
| Titanium dioxide/mica | 5.00 | — |
| Titanium dioxide/mica/iron oxide | 3.00 | — |
| Bismuth oxychloride | 10.00 | 15.00 |
| Cyclomethicone | 41.50 | 40.40 |
| Isostearyl trimethylolpropane siloxy silicate | 5.00 | 5.00 |

EXAMPLE 2

A transfer resistant lipstick composition was made according to the following formula:

|  | w/w% |
|---|---|
| Cococaprylate/caprate | 2.70 |
| Cetyl acetate:acetylated lanolin alcohol | 1.00 |
| Isostearyltrimethylol propane siloxysilicate | 7.00 |
| Methylparaben | 0.30 |
| Propylparaben | 0.10 |
| BHA | 0.10 |
| Synthetic wax | 6.60 |
| Ceresin wax | 4.00 |
| Paraffin wax | 3.00 |
| Ozokerite wax | 1.00 |
| Ellipe butter | 0.20 |
| Octyldodecanol, trilaurin phospholipids, cholesterol, glycosphingolipids | 0.50 |
| Bismuth oxychloride | 9.00 |
| Dimethicone treated mica | 2.50 |
| Mica/titanium dioxide | 2.50 |
| Cyclomethicone | 41.40 |
| Isododecanol | 9.00 |
| Polypropylene | 0.10 |
| Lanolin oil | 3.50 |
| Trioctyldodecyl citrate | 2.00 |
| pigment solids* | 3.50 |

*D & C red 7 Calcium Lake 0.90
D & C red 7 Barium Lake 2.30
FD & C yellow 6 Aluminum Lake 0.30

The above lipstick formulation was made by mixing the dry ingredients with the volatiles and silicone ester wax. Next, the waxes and oils were added with heating. The powder component was added next. The mixture was then stirred before pouring into molds and allowing to cool.

EXAMPLE 3

A transfer resistant eyeshadow, blush and concealer were made according to the following formulas:

|  | w/w% | | |
|---|---|---|---|
|  | eyeshadow | blush | concealer |
| Coco caprylate/caprate | 2.200 | 2.200 | 2.200 |
| Cetyl acetate/acetylated lanolin alcohol | 1.000 | 1.000 | 1.000 |
| Isostearyl trimethylol propanesiloxysilicate | 7.000 | 7.000 | 7.000 |
| Synthetic wax | 6.600 | 6.600 | 6.600 |
| Ceresin wax | 4.000 | 4.000 | 4.000 |
| Paraffin wax | 3.000 | 3.000 | 3.000 |
| Ozokerite | 1.000 | 1.000 | 1.000 |
| Octyldodecanol/trilaurin phospholipid/cholesterol/glycosphingolipids | 0.500 | 0.500 | 0.500 |
| Illipe butter | 0.200 | 0.200 | 0.200 |
| Polypropylene | 0.100 | 0.100 | 0.100 |
| Methyl paraben | 0.300 | 0.300 | 0.300 |
| Propyl paraben | 0.100 | 0.100 | 0.100 |
| BHA | 0.100 | 0.100 | 0.100 |
| Lanolin oil | 3.500 | 3.500 | 3.500 |
| D & C red 7 calcium lake | — | 2.100 | — |
| FD & C yellow 5 aluminum lake | — | 0.800 | — |
| Red iron oxide | 2.100 | — | 2.100 |
| Yellow iron oxide | 0.800 | — | 0.800 |
| Black iron oxide | 0.500 | 0.500 | 0.100 |
| Titanium oxide | 0.100 | 0.100 | 0.100 |
| Bismuth oxychloride | 3.000 | 3.000 | 3.000 |
| Titanium dioxide/mica | 9.000 | 9.000 | 9.000 |
| Cyclomethicone | 41.400 | 41.400 | 41.400 |
| Mica/dimethicone | 2.000 | 2.000 | 2.000 |
| Isododecane | 9.000 | 9.000 | 9.000 |
| Trioctyldodecyl citrate | 2.000 | 2.000 | 2.000 |
| cococaprylate/caprate | 0.500 | 0.500 | 0.500 |

The above cosmetic compositions were made by first mixing all of the dry ingredients. The waxes and oils were added with heating. The volatile solvent and silicone ester wax were added. The remaining ingredients were added and the mixture stirred before pouring the mixture into the appropriate molds and allowing to cool.

EXAMPLE 4

Two groups of thirty nine panelists were asked to compare the lipstick formulation of the invention ("A") with a known lipstick formulation ("B"), Revlon "Moondrops" lipstick. The first group of thirty nine panelists were asked to use lipstick "A" for one week in place of their current lipstick brand. The second group of thirty nine panelists were asked to use formulation "B" for one week in place of their current lipstick brand. The panelists were then asked a series of questions as follows:

|  | A | B |
|---|---|---|
| Did the lipstick product bleed? | | |
| Yes | 1 | 8 |
| No | 38 | 31 |
| If so, after how long? | | |
| ½ hour | — | 1 |
| 1 hour | — | 1 |
| 2 hours | — | 4 |
| Other (3–5 hours) | 1 | 2 |
| Did the lipstick leave a rim on coffee cups or cigarettes? | | |
| Yes | 15 | 36 |
| No | 24 | 3 |
| Would you consider this test lipstick to be "long wearing"? | | |
| Yes | 34 | 18 |
| No | 5 | 21 |

KISS TEST

Panelists were asked to apply the lipstick, wait 5 minutes, then kiss their hand. The panelists were then asked if the lipstick "left hardly a trace" of color on their hand. They reported as follows:

|     | A  | B  |
|-----|----|----|
| Yes | 34 | 6  |
| No  | 5  | 33 |

The above results show that the lipstick formulation of the invention exhibited superior transfer resistance when compared to a commercial lipstick formulation. Approximately 87% of the panelists agreed that lipstick "A" left hardly a trace of color on their hand whereas only 15% of panelists agreed that sample "B" (a traditional lipstick) left hardly a trace of color on their hand. The degree of improvement seen with sample A is approximately 72%.

While the invention has been described in connection with the preferred embodiment, it is not intended to limit the scope of the invention to the particular form set forth, but, on the contrary, it is intended to cover such alternatives, modifications and equivalents as may be included within the spirit and scope of the invention as defined by the appended claims.

We claim:

1. A cosmetic composition exhibiting improved transfer resistance comprising:
   a) 1–70% of a volatile solvent having a viscosity of about 0.5 to 20 centipoise at 25° C. and selected from the group consisting of volatile silicones, $C_{8-20}$ isoparaffins, and mixtures thereof,
   b) 0.1–15% of a silicone ester wax comprising moieties of the general formula:

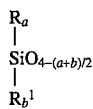

wherein R is hydrogen or methyl, $R^1$ is a carboxylic ester containing radical having 12 or more carbon atoms and comprising a carboxylic acid moiety esterified with an aliphatic alcohol moiety, a is an integer of 0 to 3 inclusive, b is an integer from 1 to 3 inclusive, and the sum of a+b has an average value of from about 1.0 to about 3.0 with the proviso that there is present at least one $R^1$ radical,
   c) 10–45% of a wax selected from the group consisting of synthetic wax, ceresin, paraffin, ozokerite, illipe butter, beeswax, carnauba, microcrystalline, lanolin, candelilla, cocoa butter, shellac wax, spermaceti, bran wax, capok wax, sugar cane wax, montan wax, whale wax, bayberry wax, and mixtures thereof,
   d) 5–50% of a powder component which is a dry, particulate matter comprised of pigments and powders having a particle size of 0.02 to 50 microns wherein the pigment to powder weight ratio ranges from 1:20 to 20:1, and
   e) 1–30% oil,
all of said percentages being based upon the total weight of the composition.

2. The composition of claim 1 wherein R is methyl.

3. The composition of claim 2 wherein the acid is a fatty acid.

4. The composition of claim 3 wherein the fatty acid has 12 or more carbon atoms.

5. The composition of claim 4 wherein the fatty acid is isostearic acid.

6. The composition of claim 4 wherein the fatty acid is lauric acid.

7. The composition of claim 1 wherein the silicone ester is a liquid.

8. The composition of claim 1 wherein the volatile solvent is a cyclic silicone having the formula:

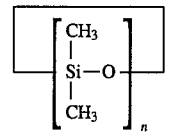

wherein n=3–7; a volatile linear polydimethylsiloxane having from 3 to 9 silicon atoms and of the general formula:

wherein n=0–7, or mixtures thereof.

9. The composition of claim 1 wherein the wax has a melting point of 35° to 120° C.

10. The composition of claim 1 wherein the oil component comprises a mixture of low viscosity and high viscosity oils.

11. The composition of claim 10 wherein the low viscosity oil has a viscosity of 5 to 100 centipoise at 25° C.

12. The composition of claim 11 wherein the high viscosity oil has a viscosity of 200 to 1,000,000 centipoise at 25° C.

13. The composition of claim 8 comprising 35–60% of a volatile solvent comprised of a mixture of cyclic silicones and $C_{8-20}$ isoparaffins.

14. The composition of claim 5 wherein the silicone ester is diisostearoyl trimethylolpropane siloxy silicate.

15. The composition of claim 6 wherein the silicone ester is dilauroyl trimethylolpropane siloxy silicate.

16. A lipstick composition having improved transfer resistance comprising, by weight of the total composition:
   a) 1–70% of a volatile solvent having a viscosity of about 0.5 to 20 centipoise at 25° C. and selected from the group consisting of volatile silicone, $C_{8-20}$ isoparaffins, and mixtures thereof,
   b) 0.1–15% of a silicone ester wax comprising moieties of the unit formula:

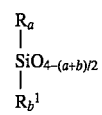

wherein R is hydrogen or methyl, $R^1$ is a carboxylic ester containing radical having 12 or more carbon atoms and comprising a carboxylic acid moiety esterified with an aliphatic alcohol moiety, a is an integer of 0 to 3 inclusive, b is an integer of 1 to 3 inclusive, and the sum of a+b has an average value of from about 1.0 to about 3.0 with the proviso that there is present at least one $R^1$ radical,
   c) 10–45% of a wax selected from the group consisting of synthetic wax, ceresin, paraffin, ozokerite, illipe butter, beeswax, carnauba, microcrystalline, lanolin, candelilla, cocoa butter, shellac wax, spermaceti, bran wax, capok wax, sugar cane wax, montan wax, whale wax, bayberry wax, and mixtures thereof,
   d) 5–50% of a powder component which is a dry, particulate matter comprised of pigments and powders having a particle size of 0.02 to 50 microns wherein the pigment to powder weight ratio ranges from 1:20 to 20:1, and c) 1–30% oil.

17. The composition of claim 16 wherein the silicone ester is diisostearoyl trimethylolpropane siloxy silicate, dilauroyl trimethylolpropane siloxy silicate, or mixtures thereof.

18. The composition of claim 16 wherein the volatile silicone is a cyclic silicone having the formula:

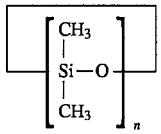

wherein n=3–7; a volatile linear polydimethylsiloxane having from 3 to 9 silicone atoms and of the general formula:

wherein n=0–7, or mixtures thereof.

19. The composition of claim 16 wherein the oil component comprises a mixture of low viscosity and high viscosity oils.

20. The composition of claim 19 wherein the low viscosity oil has a viscosity of 5 to 100 centipoise at 25° C.

21. The composition of claim 20 wherein the high viscosity oil has a viscosity of 200 to 1,000,000 centipoise at 25° C.

22. The composition of claim 21 wherein the weight ratio of low viscosity to high viscosity oils in the oil phase is 1:15 to 15:1.

23. The lipstick of claim 16 wherein the volatile solvent is cyclomethicone.

24. The lipstick of claim 23 wherein the cyclomethicone is present as 35–60% by weight of the composition.

25. The composition of claim 1 wherein the silicone ester wax is a siloxy silicate.

26. The composition of claim 4 wherein the silicone ester wax is a siloxy silicate.

27. The composition of claim 4 wherein the fatty acid moiety is separated from the silicon atom by the aliphatic alcohol moiety.

28. The composition of claim 27 wherein the fatty acid moiety has 12 to 18 carbon atoms.

29. The lipstick composition of claim 17 wherein the composition contains 3–10 wt. % of silicone ester wax.

30. The lipstick composition of claim 29 wherein the pigment constitutes 5–50 wt. % of the composition.

31. The lipstick composition of claim 29 wherein the the powder constitutes about 10–20 wt. % of the composition and the pigment constitutes about 1–10 wt. % of the composition.

32. The lipstick composition of claim 19 wherein the low viscosity oil has a viscosity of 5 to 100 centipoise at 25° C., the high viscosity oil has a viscosity of 100,000 to 250,000 centipoise at 25° C., the weight ratio of low viscosity oil to high viscosity oil is 1:10 to 10:1, and the oil component constitutes 1 to 20 wt. % of the composition.

33. A lipstick composition exhibiting improved transfer resistance comprising:

a) 1–70% cyclomethicone, b) 0.1–15% of a silicone ester wax comprising moieties of the general formula:

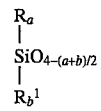

wherein R is methyl, $R^1$ is a carboxylic ester-containing radical comprising a fatty acid moiety esterified with an aliphatic alcohol moiety, the fatty acid moiety having 12 or more carbon atoms and being separated from the silicon atom by the aliphatic alcohol moiety, a is an integer of 0 to 3 inclusive, b is an integer from 1 to 3 inclusive, and the sum of a+b has an average value of from about 1.0 to 3.0 with the proviso that there is present at least one $R^1$ radical, said silicone ester wax having a melting point of up to 90° C., c) 10–45% of a wax having a melting point in the range of 35° to 120° C., and being selected from the group consisting of synthetic wax, ceresin, paraffin, ozokerite, illipe butter, beeswax, carnauba, microcrystalline, lanolin, candelilla, cocoa butter, shellac wax, spermaceti, bran wax, shellac wax, capok wax, sugar cane wax, montan wax, whale wax, bayberry wax, and mixtures thereof, d) a powder component which is a dry, particulate matter comprised of pigment and non-colored powder having a particle size of 0.02 to 50 microns, wherein the pigment-to-powder weight ratio ranges from 1:20 to 20:1, the pigment constitutes 1–10% of the composition, and the non-colored powder constitutes about 10–20% of the composition, and e) 1–20% oil, all of said percentages being based on the total weight of the composition.

* * * * *

UNITED STATES PATENT AND TRADEMARK OFFICE
CERTIFICATE OF CORRECTION

PATENT NO. : 5,505,937

DATED : April 9, 1996

INVENTOR(S) : Castrogiovanni, et al.

It is certified that error appears in the above-identified patent and that said Letters Patent is hereby corrected as shown below:

In column 2, line 51. after "(also called" delete "dilaurolyl" and insert therefor --dilauroyl--.

On the title page: Item [56] in the "References Cited" Section, please add the following:

U.S. PATENT DOCUMENTS

| | | |
|---|---|---|
| 3,764,537 | 1973 | MacLeod |
| 3,857,805 | 1974 | Prickril |
| 4,578,266 | 3/1986 | Tietjen |
| 4,725,658 | 2/1988 | Thayer |
| 4,736,048 | 1988 | Brown |
| 4,980,440 | 1990 | Kendziorski |
| 5,051,489 | 1991 | O'Lenick |
| 5,087,443 | 2/1992 | Chizat |
| 5,250,202 | 1993 | Reinehr |
| 5,334,737 | 8/1994 | Thimineur |
| 5,422,412 | 1995 | Morita |

UNITED STATES PATENT AND TRADEMARK OFFICE
CERTIFICATE OF CORRECTION

PATENT NO. : 5,505,937

DATED : April 9, 1996

INVENTOR(S) : Castrogiovanni, et. al.

It is certified that error appears in the above-identified patent and that said Letters Patent is hereby corrected as shown below:

FOREIGN PATENT DOCUMENTS

| | | |
|---|---|---|
| 0135060 | 7/1984 | Europe |
| 0255843 | 2/1988 | Europe |
| 0462709 | 12/1991 | Europe |
| 0486394 | 5/1992 | Europe |
| 0590192 | 4/1994 | Europe |
| 2014852 | 9/1979 | United Kingdom |
| 317302 | 12/1956 | Germany |
| 93/17660 | 4/1993 | WIPO |

OTHER PUBLICATIONS

Information about Silicone Fluids, Dow Corning Corp., 1982

Reprint: Kirk-Othmer Encyclopedia of Chemical Technology, Vol. 20, 3rd Edition, 1982

CTFA Cosmetic Ingredient Handbook, First Edition, 1988.

The HAPPI Article, "Novel Silicone Esters for Cosmetics", Virginia Van Valkenburgh and Raymond Thimineur, 9/1992

The DCI Article, "Novel Silicones For Skin Care Products", Ray Thimineur, 1/1992

GE Silicones - Data Sheet - 4/1992

UNITED STATES PATENT AND TRADEMARK OFFICE
CERTIFICATE OF CORRECTION

PATENT NO. : 5,505,937
DATED : April 9, 1996
INVENTOR(S) : Castrogiovanni, et al.

It is certified that error appears in the above-identified patent and that said Letters Patent is hereby corrected as shown below:

OTHER PUBLICATIONS (cont'd)

Chem. Abstracts 93: 79880 - JP 55028906, 800229, JP 78-100785 78-818

Chem. Abstracts 105: 213946 - JP 61161211, AZ 860721, JP 85-2857 85011 7/1986

Chem. Abstracts 105: 120498 - JP 61065809 AZ 86-404, JP

Chem. Abstracts 105: 213941 - JP 61158913 AZ 860718, JP 84-279161 84 1229 7/1986

Chem. Abstracts 110: 121023 - JP 62298512 AZ 871225 JP 86-143759 860619 12/1987

Tenside Surf. Det. 27 (1990) p. 154-158 1/1990

Signed and Sealed this

Fifteenth Day of October, 1996

Attest:

BRUCE LEHMAN

Attesting Officer

Commissioner of Patents and Trademarks